US006495733B1

(12) United States Patent
Peratello et al.

(10) Patent No.: US 6,495,733 B1
(45) Date of Patent: Dec. 17, 2002

(54) SUPERACID CATALYST FOR THE HYDROISOMERIZATION OF N-PARAFFINS

(75) Inventors: Stefano Peratello, Milan (IT); Angela Carati, Milan (IT)

(73) Assignees: AGIP Petroli S.p.A., Rome (IT); Enitecnologie S.p.A., San Donato Milanese (IT)

(*) Notice: Subject to any disclaimer, the term of this patent is extended or adjusted under 35 U.S.C. 154(b) by 0 days.

(21) Appl. No.: 09/673,644

(22) PCT Filed: Jul. 15, 1999

(86) PCT No.: PCT/EP99/05044

§ 371 (c)(1),
(2), (4) Date: Oct. 10, 2000

(87) PCT Pub. No.: WO00/03801

PCT Pub. Date: Jan. 27, 2000

(30) Foreign Application Priority Data

Jul. 16, 1998 (IT) .......................................... MI98A1630

(51) Int. Cl.[7] ...................... B01J 27/053; B01J 27/045; B01J 23/44; C07C 5/13
(52) U.S. Cl. ...................... 585/743; 585/750; 585/751; 502/217; 502/223; 502/339; 502/349
(58) Field of Search ................................. 585/750, 751, 585/743; 502/217, 223, 339, 349

(56) References Cited

U.S. PATENT DOCUMENTS 6,037,303 A * 3/2000 Peratello et al. ............ 502/217

OTHER PUBLICATIONS

Tichit; "one step sol–gel synthesis of sulfated–zirconia catalysts"; 1995; Baltzer AG, Science Publishers; pp. 109–113.*

* cited by examiner

Primary Examiner—Thuan D. Dang
(74) Attorney, Agent, or Firm—Oblon, Spivak, McClelland, Maier & Neustadt, P.C.

(57) ABSTRACT

A superacid catalyst comprising: zirconium oxide on whose surface sulfate groups are present, in a quality corresponding to total coverage of the surface of the zirconium oxide by means of a monolayer of these sulfate groups, optionally containing a noble metal in a quantity ranging from 0.1 to 3% by weight, with a porosity ranging from 0.1 to 0.30 $cm^3/g$, consisting of at least 70% of pores with a diameter ranging from 1 to 4 nm, prepared by a process which comprises:

Figure 1:
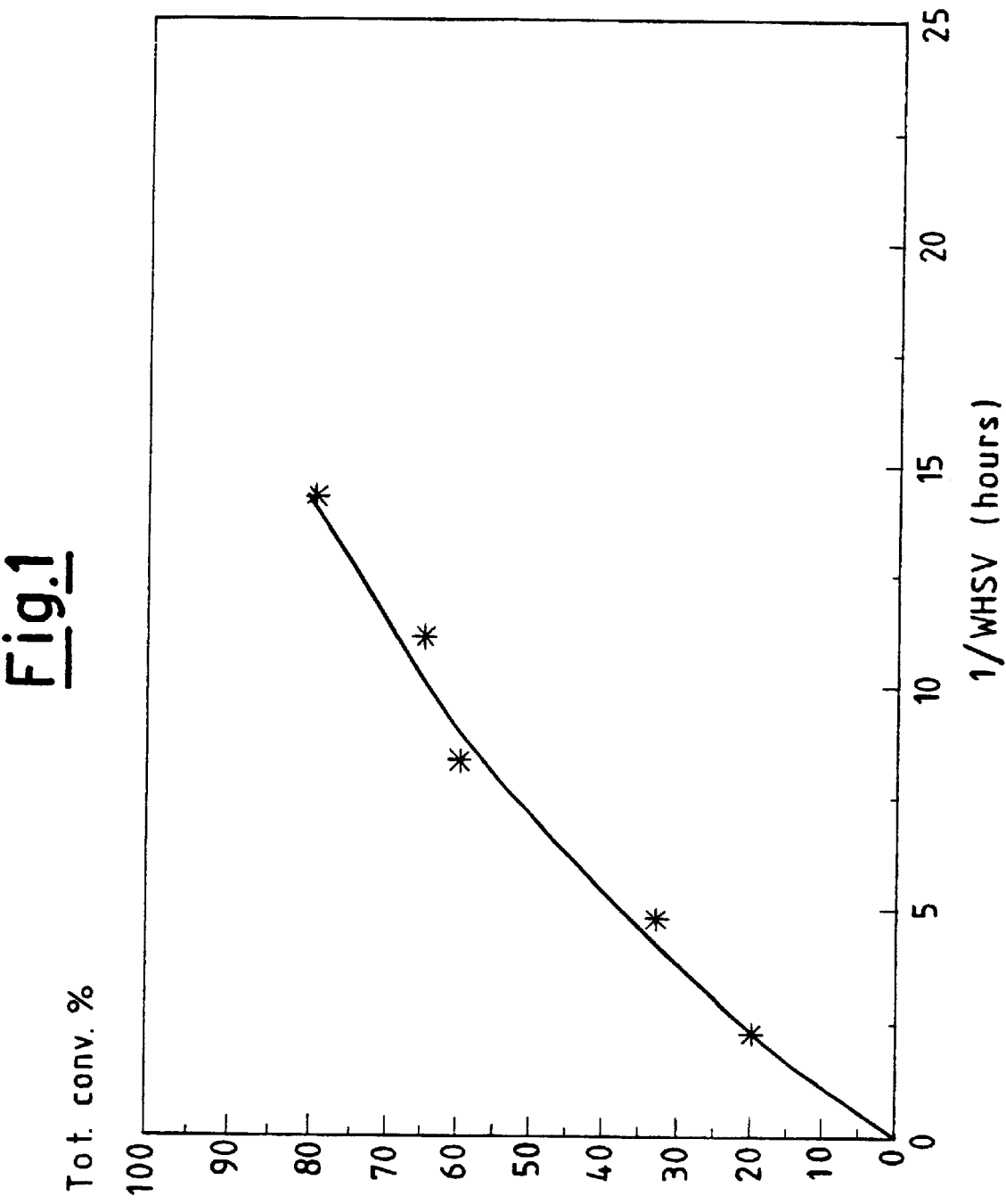

(a) hydrolyzing derivate of zirconium in a basic medium in the presence of a tetra-alkylammonium hydroxide (TAA), sulfuric acid and acetylacetone (AcAc);

(b) drying the product of step (a) and calcining the dried material at a temperature ranging from 250 to 650° C.

(c) optionally treating the product resulting from step (b) with an aqueous solution of a compound of a noble metal, and drying and calcining the treated product.

20 Claims, 1 Drawing Sheet

SUPERACID CATALYST FOR THE HYDROISOMERIZATION OF N-PARAFFINS

BACKGROUND OF THE INVENTION

1. Field of the Invention

The present invention relates to a superacid catalyst based on sulfated zirconium oxide, optionally containing a noble metal, prepared in the presence of acetylacetone. This catalyst is useful in acid-catalyzed processes and in the hydroisomerization of n-paraffins.

2. Description of the Background

Catalysts based on sulfated oxides of zirconium, titanium, iron having superacid characteristics, are known in the art, according to the definition of Gillespie, as described for example by K. Arata, Adv. Catal., 37, 165, 1990. These superacid catalysts are usually prepared by means of an articulate synthesis comprising numerous steps. For example sulfated zirconia ($ZrO_2/SO_4^{-2}$) is generally prepared in the following way:

1) precipitation of fresh zirconia hydroxide;
2) drying;
3) impregnation with a sulfating agent;
4) calcination.

Step (3) can be carried out in various ways: via wet inbibition point, as described in EP 520 543, by treatment with a gaseous stream of $H_2S$ or $SO_2$, as described by J. R. Shon, H. W. Kim, in J. Mol. Catal., 52, (1989), 361, or by treatment in solution (R. Le Van Mao, S. Xiao and T. Si Le, Catal. Lett., 35, (1995), 107; D. Farcasiu, J. Qi Li, in Appl. Cat. A, 128, (1995), 97). All the steps of this preparation are critical: zirconium precursor, drying temperature, sulfating agent, concentration of the sulfating agent solution used, temperature and calcination time. As a result the control and reproducibility of the synthesis are complicated. Simplified syntheses of $ZrO_2/SO_4^{2-}$ comprising a single synthesis step have recently been effected. For example H. Arata et al. use $Zr(SO_4)_2$ as precursor (Bull. Chem. Soc.Jpn., 63, (1990), 244): this method however does not allow control of the sulfur content and its dispersion. U. Ciesla et al. precipitate zirconium hydroxide in the presence of alkyl sulfonates or sulfonates (EUROPACAT II Congress 3–8 September 1995). The crystallization of the amorphous phase begins at very high temperatures, higher than 650° C. Another synthesis method in a single step is based on the gelation of $Zr(OC_3H_7)_4$ dispersed in propaol, nol, in an acid environment by $HNO_3/H_2SO_4$. The material, before being calcined, must be dried under supercritical conditions (D. A. Ward, E. I. Ko. J.Cat. 150, (1994), 18).

In D. Tichit et al., Catal. Let., 38 (1996) 109–113, $Zr(OC_3H_7)_4$ dispersed in propanol, is gelified in an acid environment by $H_2SO_4$. The materials obtained after calcination at 650° C. consist of tetragonal phase associated with small quantities of monoclinic phase. Patent application MI 97A00358 describes a sulfated zirconia catalyst with particular porosity characteristics and with high acid properties prepared by means of a process in a single reaction step. This superacid catalyst comprising zirconium oxide on the surface of which sulfate groups are present in a quantity corresponding to total coverage of the surface of the zirconium oxide by means of a monolayer of these sulfate groups, is characterized by a porosity ranging from 0.1 to 0.3 $cm^3/g$ consisting of at least 70% of pores having a diameter ranging from 1 to 4 nm. According to a preferred aspect, this material may additionally contain a noble metal, preferably platinum, in a quantity ranging from 0.1 to 3% by weight.

These materials are prepared by means of a process which comprises:

(a) hydrolysis in an alkaline environment of a hydrolyzable compound of zirconium in the presence of a tetra-alkylammonium hydroxide (TAA) and sulfuric acid
(b) drying of the resulting product and its calcination at a temperature ranging from 250 to 650° C.

The materials obtained in step (b) can be impregnated with a solution of a compound of a noble metal to obtain a sulfated zirconia on whose surface a noble metal is deposited in a quantity that varies from 0.1 to 3% by weight. The presence of superacid sites in these materials was verified by pyridine absorption and FT-IR spectrum analysis. It is specified in fact by K. Tanabe et al., Successful Design of Catalysts, T. Inui Ed., (1988), 616, that sulfated zirconia has an intense IR band at about 1370 $cm^{-1}$, attributed to the asymmetrical stretching of the S=O group. The absorption of pyridine causes a consistent shift of this signal and the entity of this shift is correlated to the superacid strength of the material and its catalytic properties. The material described in MI 97A00358 showed a shift ranging from 50 to 60 $cm^{-1}$ against a maximum value provided in literature of 50 $cm^{-1}$.

These catalysts based on sulfated zirconia are superacid solids and can therefore be used in acid-catalyzed reactions. When they additionally contain a noble metal they are bifunctional catalysts that can be used in the hydroisomerization process of n-paraffins, to convert these hydrocarbons with a linear chain to hydrocarbons with a branched chain. According to a preferred aspect, light n-paraffins can be particularly subjected to hydroisomerization to obtain hydrocarbons with a branched chain having a higher octane number, for use as fuels.

SUMMARY OF THE INVENTION

We have now unexpectedly found that by carrying out the synthesis of this sulfated zirconia in the presence of acetylacetone, catalysts based on zirconium oxide are obtained, on whose surface sulfate groups are present with improved superacid characteristics and which are therefore more active in acid-catalyzed reactions.

The present invention therefore relates to a superacid catalyst comprising zirconium oxide on whose surface sulfate groups are present, in a quantity corresponding to total coverage of the surface of the zirconium oxide by means of a monolayer of these sulfate groups, having a porosity ranging from 0.1 to 0.30 $cm^3/g$, consisting of at least 70% of pores with a diameter ranging from 1 to 4 nm, optionally containing a noble metal in a quantity ranging from 0.1 to 3% by weight, obtained by means of:

(a) hydrolysis in an alkaline environment of a hydrolyzable compound of zirconium in the presence of a tetra-alkylammonium hydroxide (TAA) and sulfuric acid and acetylacetone;
(b) drying of the resulting product and calcination at a temperature ranging from 250 to 650° C.;
(c) optional treatment of the product resulting from step (b) with an aqueous solution of a compound of a noble metal, drying and calcination.

The presence in step (a) of the synthesis of acetylacetone (AcAc) allows the preparation of sulfated zirconia with improved superacid characteristics, and therefore more active in acid-catalyzed reactions.

DETAILED DESCRIPTION OF THE PREFERRED EMBODIMENTS

In step (a) of the preparation process of the material of the present invention the tetra-alkylammonium hydroxide is selected from hydroxides of the type $R_1R_2R_3R_4NOH$, wherein $R_1$, $R_2$, $R_3$ and $R_4$ are the same or different and are alkyl groups, preferably comprising from 1 to 6 carbon atoms; the hydrolyzable derivative of zirconium is selected from alkoxyderivatives, nitrate, sulfate, and is preferably tetrapropylorthozirconate. The sulfuric acid is used in aqueous solution in a concentration ranging from 0.01 to 10 M. The molar ratios of the mixture of step (a) are the following:

AcAc/Zr=0.001–0.5

TAA/Zr=0.05–0.25

ROH/Zr=10–100

$H_2SO_4$/Zr=0.1–0.5

$H_2O$/Zr=2–100

According to a preferred aspect the zirconium compound is dispersed in an alcohol ROH wherein R is an alkyl with from 1 to 6 carbon atoms, and is preferably propanol; the acetylacetone is then added to this mixture followed by the tetra-alkylammonium hydroxide in aqueous solution, preferably tetrapropylammonium hydroxide, and the resulting solution is left under stirring for a few hours before adding the sulfuric acid solution. The resulting dense slurry, which must have a basic pH, is left under stirring for a period of time ranging from 2–20 hours.

In step (b) the resulting product, after possible concentration, is dried to a temperature ranging from 80 to 150° C. and is then calcined at a temperature ranging from 250 to 650° C., preferably from 400 to 600° C.

According to a preferred aspect the catalytic material of the present invention may additionally contain a noble metal, preferably platinum, in a quantity ranging from 0.1 to 3% by weight. These catalysts are prepared by treatment of the material obtained in the previous step (b) with an aqueous solution of a compound of a noble metal, drying and calcination. Preferably, the material obtained in step (b) is impregnated by means of the "wet inhibition" method which is well known in the art, with an aqueous solution of a compound of a noble metal, preferably platinum, to deposit a quantity of noble metal ranging from 0.1 to 3% by weight. Hexachloroplatinic acid and ammonia complexes of tetravalent platinum are preferred for the purposes. This is followed by drying at a temperature ranging from 80° to 150° C. and calcination at a temperature ranging from 400° to 600° C.

The materials of the present invention are completely crystalline to X-rays and consist of tetragonal zirconia crystallites having dimensions of less. than 300 Å, generally between 50 and 150 Å. The surface area of these materials is greater than 30 m$^2$/g, preferably between 60 and 120 m$^2$/g. The content of sulfates can be determined by chemical analysis and corresponds to the theoretical value which can be calculated for the total coverage of the zirconia surface by means of a monolayer of sulfate groups, as described by P. Nascimento et al., in "New Frontiers in Catalysis", Proceedings of the 10th International Congress on Catalysis (L. Guczi et al. EDS.) p. 1185, Elsevier (1993). For a surface area between the preferred values previously indicated, the sulfur content in the catalyst, corresponding to a monolayer of sulfate groups, is between 1 and 3% by weight.

The sulfate groups are attached to the zirconia by means of the hydroxyls present on its surface, and therefore the possibility of obtaining a monolayer of sulfates, corresponding to the maximum acidity of the material, is linked to the presence of a sufficient number of hydroxyls on the surface of the zirconia.

The catalysts based on sulfated zirconia of the present invention are superacid solids which are more active than the sulfated zirconia prepared as described in MI 97A00358, i.e. without the presence of acetylacetone in the synthesis mixture. They are materials which can be used in acid-catalyzed reactions and in particular, when they additionally contain a noble metal, they are bifunctional catalysts with an improved activity in the hydroisomerization process of n-paraffins, to convert these hydrocarbons with a linear chain into hydrocarbons with a branched chain, i.e. they give much higher conversions and comparable selectivities with respect to the sulfated zirconia prepared without acetylacetone.

According to a preferred aspect, the best results can be particularly obtained when light n-paraffins containing from 4 to 10 carbon atomsare subjected to hydroisomerization to obtain hydrocarbons with a branched chain having a higher octane number, for use as fuels.

By subjecting $C_5$–$C_6$ n-paraffins, or a mixture thereof, to hydroisomerization, as the Light straight run fraction deriving from topping, light gasolines are obtained with a high octane number. By subjecting, on the other hand, $C_6$–$C_8$ n-paraffins, or their mixtures, to hydroisomerization, it is possible to obtain heavy gasolines with a high octane number.

The operation is carried out in the presence of hydrogen, at a temperature ranging from 250 to 300° C., preferably between 50 and 130° C., and at a pressure ranging from 5 to 80 bars, preferably between 20 and 50 bars. The noble metal is preferably platinum. The WHSV space velocity (hours$^{-1}$), expressed as g paraffin/g catalyst hours, is between 0.01 and 1, and the molar ratio hydrogen/paraffin is between 5 and 30.

According to another aspect, these bifunctional catalysts can be used in hydroisomerization processes of waxes (n-paraffins with a number of carbon atoms equal to or greater than 12) to improve the pour point and viscosity index, to obtain bases for lubricating oils.

EXAMPLE 1

66 g of $Zr(OC_3H_7)_4$ at 70% by weight in propanol, 0.14 g of acetylacetone and 10 g of tetrapropylammonium hydroxide at 40% by weight in aqueous solution are added to 364 g of n-$C_3H_7OH$. After two hours of aging under stirring, 50 g of an aqueous solution of $H_2SO_4$ 0.44 M are added. The mixture is left under stirring for four hours at room temperature, then a further 4 hours at 600° C. The sample is dried for 8 hours at 100° C. and is then calcined for 5 hours at 550° C. The material obtained after calcination consists of a pure tetragonal phase, with crystallites having an average diameter of 90 Å, a surface area of 74 m$^2$/g, a pore volume of 0.1 cm$^3$/g. Porosity below 10 Å and over 40 Å is not present.

The final sulfur content determined by chemical analysis is 1.5% which corresponds to a total monolayer surface coverage of sulfate groups.

EXAMPLE 2

10 g of the material prepared in example 1 are impregnated with the wet inbibition point technique with 1.6 ml of an aqueous solution of $H_2PtCl_6$ containing .031 g of Pt per ml.

The resulting product is dried at 100° C. and calcined at 550° C.

A catalyst is obtained with a total Pt content of 0.5% by weight.

EXAMPLE 3

10 g of the material prepared in example 1 are impregnated with the wet inbibition point technique with 1.6 ml of an aqueous solution of $H_2PtCl_6$ containing 0.063 g of Pt per ml.

The resulting product is dried at 100° C. and calcined at 550° C.

A catalyst is obtained with a total Pt content of 1% by weight.

EXAMPLE 4 (comparative)

A sulfated zirconia is prepared as described in MI97A0038: 33 g of $Zr(OC_3H_7)_4$ at 70% by weight in propanol and 5 g of tetrapropylammonium hydroxide at 40% by weight in aqueous solution are added to 182 g of n-$C_3H_7OH$. After two hours of aging under stirring, 25 g of an aqueous solution of $H_2SO_4$ 0.44 M are added. The mixture is left under stirring for four hours at room temperature, then a further 4 hours at 600° C. The sample is dried for 8 hours at 100° C. and is then calcined for 5 hours at 550° C. The material obtained after calcination consists of a pure tetragonal phase, with crystallites having a diameter of 85 Å, a surface area of 103 m$^2$/g, a pore volume of 0.162 cm$^3$/g with a distribution of the pore diameter centered on 35 Å.

The final sulfur content determined by chemical analysis is 1.7% which corresponds to the total mono layer surface coverage of sulfate groups.

EXAMPLE 5 (comparative)

10 g of the material prepared in example 4 are impregnated with the wet inbibition point technique with 1.6 ml of an aqueous solution of $H_2PtCl_6$ containing 0.031 g of Pt per ml.

The resulting product is dried at 100° C. and calcined at 550° C.

A catalyst is obtained with a total Pt content of 0.5% by weight.

EXAMPLE 6 (comparative)

10 g of the material prepared in example 4 are impregnated with the wet inbibition point technique with 1.6 ml of an aqueous solution of $H_2PtCl_6$ containing 0.063 g of Pt per ml.

The resulting product is dried at 100° C. and calcined at 550° C.

A catalyst is obtained with a total Pt content of 1% by weight.

EXAMPLE 7 (catalytic test)

A sample of catalyst synthesized as described in example 2. is charged into a fixed-bed tubular reactor and tested in the hydroisomerization reaction of n-heptane, under the following operating conditions:

T=100° C.
P $H_2$=50 bars
$H_2$/n-$C_7$=18 mol/mol
1/WHSV=1–15 hours

FIG. 1 indicates the conversion of n-heptane in relation to the contact time expressed as 1/WHSV. The WHSV parameter is calculated as (g of n-$C_7$)/(cat. hours). The hydroisomerization products obtained are: methylhexanes, dimethylpentanes and trimethylbutanes. The selectivity to hydroisomerization is higher than 90%.

What is claimed is:

1. A superacid catalyst having a porosity ranging from 0.1 to 0.30 cm$^3$/g, consisting of at least 70% of pores with a diameter ranging from 1 to 4 nm, comprising zirconium oxide consisting of crystallites of pure tetragonal phase with dimension of less than 300 Angstroms, the zirconium oxide surface having sulfate groups thereon in a quantity corresponding to the total coverage of the surface of zirconium oxide by a monolayer of said sulfate groups, obtained by means or a process which comprises:
    (a) hydrolyzing a hydrolyzable derivative of zirconium in a basic medium in the presence of a tetra-alkylammonium hydroxide (TAA), sulfuric acid and acetylacetone (AcAc);
    (b) drying the product of step (a) and calcining the dried material at a temperature ranging from 250 to 650° C.;
    (c) optionally treating the product resulting from step (b) with an aqueous solution of a compound of a noble metal, and drying and calcining the treated product.

2. The catalyst according to claim 1, having a surface area ranging from 60 to 120 m$^2$/g and a sulfur content by weight, with respect to the weight of the catalyst, ranging from 1 to 3%.

3. The catalyst according to claim 1, wherein the noble metal is platinum.

4. The catalyst according to claim 1, wherein the alkyl groups of the tetra-alkylammonium hydroxide, each are the same or different.

5. The catalyst according to claim 4, wherein the alkyl groups contain from 1 to 6 carbon atoms.

6. The catalyst according to claim 5, wherein the tetra-alkylammonium hydroxide is tetrapropylammonium hydroxide.

7. The catalyst according to claim 1, wherein the hydrolyzable derivative of zirconium is alkoxy, nitrate and sulfate derivatives.

8. The catalyst according to claim 7, wherein the hydrolyzable derivative of zirconium is tetrapropylorthozirconate.

9. The catalyst according to claim 1, wherein the sulfuric acid is used in aqueous solution with a concentration ranging from 0.01 to 10 M.

10. The catalyst according to claim 1, wherein the molar ratios in the mixture in step (a) are the following:

AcAc/Zr=0.001–0.5
TAA/Zr=0.05–0.25
ROH/Zr=10–100
$H_2SO_4$/Zr=0.1–0.5
$H_2O$/Zr=2–100.

11. The catalyst according to claim 1, wherein in step (c) the material obtained in step (b) is impregnated with from 0.1 to 3% by weight of a noble metal from an aqueous solution containing a noble metal compound by the "wet inhibition" method.

12. A method of performing an acid catalyzed reaction, comprising:
    conducting the reaction comprising reactants of the reaction in the presence of the superacid catalyst of claim 1.

13. A process of hydroisomerization of n-paraffins, comprising:
    contacting an n-paraffin, or a mixture of n-paraffins under hydroisomerization conditions with a superacid catalyst containing a noble metal according to claim 1, thereby producing an isomerized product of the n-paraffin or mixture of paraffins.

14. The process according to claim 13, wherein the n-paraffin is a paraffin having from 4 to 10 carbon atoms.

15. The process according to claim 13, which comprises conducting the reaction in the presence of hydrogen at a temperature ranging from 25° to 300° C., at a WHSV space velocity (hours$^{-1}$), expressed as g paraffin/g cat. hours, ranging from 0.01 to 1, at a molar ratio of hydrogen/paraffin ranging from 5 to 30 and at a pressure ranging from 5 to 80 bars.

16. The process according to claim 15, wherein the temperature ranges from 50 to 130° C. and the pressure ranges from 20 to 50 bars.

17. The process according to claim 13, wherein the n-paraffin contains from 5 to 6 carbon atoms.

18. The process according to claim 13, wherein the n-paraffin contains from 7 to 9 carbon atoms.

19. The process according to claim 13, wherein the n-paraffin is a wax.

20. A superacid catalyst having a porosity ranging from 0.1 to 0.30 cm$^3$/g, consisting of at least 70% of pores with a diameter ranging from 1 to 4 nm, comprising zirconium oxide consisting of crystallites of pure tetragonal phase with dimension of less than 300 Angstroms, the zirconium oxide surface having sulfate groups thereon in a quantity corresponding to the total coverage of the surface of zirconium oxide by a monolayer of said sulfate groups, obtained by means or a process which comprises:

(a) hydrolyzing a hydrolyzable derivative of zirconium in a basic medium in the presence of a tetra-alkylammonium hydroxide (TAA) and acetylacetone (AcAc);

(b) treating the medium containing hydrolyzed material of step (a) with sulfuric acid, with the medium remaining basic;

(c) drying the product of step (a) and calcining the dried material at a temperature ranging from 250 to 650° C.;

(d) optionally treating the product resulting from step (b) with an aqueous solution of a compound of a noble metal, and drying and calcining the treated product.

* * * * *

UNITED STATES PATENT AND TRADEMARK OFFICE
CERTIFICATE OF CORRECTION

PATENT NO. : 6,495,733 B1
DATED : December 17, 2002
INVENTOR(S) : Peratello et al.

It is certified that error appears in the above-identified patent and that said Letters Patent is hereby corrected as shown below:

<u>Title page,</u>
Item [86], the PCT information should read:
-- [86]  PCT No.:     PCT/EP99/05044

§ 371 (c)(1),
(2), (4) Date:    Oct. 31, 2000 --
Item [30], Foreign Application Priority Data, should read:
-- [30]         Foreign Application Priority Data
    Jul. 16, 1998    (IT) ………………………….MI98A001630 --

Signed and Sealed this

Twenty-ninth Day of April, 2003

JAMES E. ROGAN
*Director of the United States Patent and Trademark Office*